(12) United States Patent
Shea et al.

(10) Patent No.: US 9,848,989 B2
(45) Date of Patent: Dec. 26, 2017

(54) ORTHOPEDIC AUGMENTS HAVING RECESSED POCKETS

(71) Applicant: Smith & Nephew, Inc., Memphis, TN (US)

(72) Inventors: Jeffrey J. Shea, Memphis, TN (US); Daniel R. Goldberg, Memphis, TN (US); Nathaniel M. Quinn, Arlington, TN (US); Stanley Tsai, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/163,190

(22) Filed: May 24, 2016

(65) Prior Publication Data

US 2016/0262895 A1 Sep. 15, 2016

Related U.S. Application Data

(63) Continuation of application No. 14/185,444, filed on Feb. 20, 2014, now Pat. No. 9,345,576, which is a
(Continued)

(51) Int. Cl.
*A61F 2/34* (2006.01)
*A61F 2/46* (2006.01)
(Continued)

(52) U.S. Cl.
CPC ............ *A61F 2/34* (2013.01); *A61F 2/30734* (2013.01); *A61F 2/4601* (2013.01);
(Continued)

(58) Field of Classification Search
CPC ...... A61F 2/32; A61F 2/34; A61F 2/30; A61F 2002/3225; A61F 2002/3208;
(Continued)

(56) References Cited

U.S. PATENT DOCUMENTS 2,874,003 A 4/1975 Moser et al.
3,882,550 A 5/1975 Karpf et al.
(Continued)

FOREIGN PATENT DOCUMENTS

DE 202011050057 U1 7/2011
DE 202011050057 U1 9/2011
(Continued)

OTHER PUBLICATIONS

Australian Examination Report; Australian Patent Office; Australian Patent Application No. 2012347730; dated Aug. 12, 2016; 3 pages.
(Continued)

*Primary Examiner* — Alvin Stewart
(74) *Attorney, Agent, or Firm* — Taft Stettinius & Hollister LLP

(57) ABSTRACT

Systems, devices, and methods for providing orthopedic augments having recessed pockets that receive a fixation material. The orthopedic augments include an outer surface that interfaces with a patient's tissue or bone, and an inner surface that interfaces with an implant, the inner surface defining a recessed pocket configured to receive a fixation material, a rim around at least a portion of the recessed pocket, and a port in the rim, wherein the recessed pocket extends along the inner surface in at least a direction laterally from the port.

20 Claims, 8 Drawing Sheets

Related U.S. Application Data continuation of application No. PCT/US2012/068304, filed on Dec. 6, 2012.

(60) Provisional application No. 61/568,023, filed on Dec. 7, 2011.

(51) Int. Cl.
    *A61F 2/30* (2006.01)
    *A61B 17/80* (2006.01)

(52) U.S. Cl.
    CPC ........ *A61B 17/8052* (2013.01); *A61F 2/30723* (2013.01); *A61F 2002/3069* (2013.01); *A61F 2002/30449* (2013.01); *A61F 2002/30581* (2013.01); *A61F 2002/30583* (2013.01); *A61F 2002/30589* (2013.01); *A61F 2002/30593* (2013.01); *A61F 2002/30736* (2013.01); *A61F 2002/30919* (2013.01); *A61F 2002/4631* (2013.01); *A61F 2220/0016* (2013.01)

(58) Field of Classification Search
    CPC .... A61F 2002/3414; A61F 2002/30242; A61F 2002/30378; A61F 2002/3433; A61F 2/30734; A61F 2/30736
    USPC .......... 623/23.19–23.2, 19.11–19.14
    See application file for complete search history.

(56) References Cited

U.S. PATENT DOCUMENTS

| | | | |
|---|---|---|---|
| 3,894,297 | A | 7/1975 | Mittelmeier et al. |
| 4,141,088 | A | 2/1979 | Treace et al. |
| 4,437,193 | A | 3/1984 | Oh |
| 4,473,068 | A | 9/1984 | Oh |
| 4,475,549 | A | 10/1984 | Oh |
| 4,566,138 | A | 1/1986 | Lewis et al. |
| 4,612,160 | A | 9/1986 | Donlevy et al. |
| 4,623,352 | A | 11/1986 | Oh |
| 4,632,111 | A | 12/1986 | Roche |
| 4,666,450 | A | 5/1987 | Kenna |
| 4,673,409 | A | 6/1987 | Van Kampen |
| 4,676,799 | A | 6/1987 | Legrand |
| 4,704,127 | A | 11/1987 | Averill et al. |
| 4,718,908 | A | 1/1988 | Wigginton et al. |
| 4,795,469 | A | 1/1989 | Oh |
| 4,883,490 | A | 11/1989 | Oh |
| 4,888,022 | A * | 12/1989 | Huebsch ............ A61B 17/8822 623/23.19 |
| 4,888,024 | A * | 12/1989 | Powlan ............. A61B 17/8808 623/23.19 |
| 4,892,550 | A * | 1/1990 | Huebsch ............... A61F 2/4637 623/23.19 |
| 4,904,265 | A | 2/1990 | MacCollum et al. |
| 4,955,919 | A | 9/1990 | Pappas et al. |
| 4,959,072 | A | 9/1990 | Morscher et al. |
| 4,990,149 | A | 2/1991 | Fallin |
| 4,995,883 | A | 2/1991 | Demane et al. |
| 4,997,447 | A | 3/1991 | Shelley |
| 5,047,033 | A | 9/1991 | Fallin |
| 5,078,746 | A | 1/1992 | Garner |
| 5,080,677 | A | 1/1992 | Shelley |
| 5,108,452 | A | 4/1992 | Fallin |
| 5,133,764 | A | 7/1992 | Pappas et al. |
| 5,133,767 | A * | 7/1992 | Frey .................. A61B 17/8808 623/23.54 |
| 5,176,711 | A * | 1/1993 | Grimes ............. A61B 17/1666 623/22.22 |
| 5,192,329 | A | 3/1993 | Christie et al. |
| 5,193,679 | A | 3/1993 | White |
| 5,211,665 | A | 5/1993 | Ku |
| 5,217,499 | A | 6/1993 | Shelley |
| 5,226,917 | A | 7/1993 | Schryver |
| 5,310,408 | A | 5/1994 | Schryver et al. |
| 5,314,487 | A | 5/1994 | Schryver et al. |
| 5,324,291 | A | 6/1994 | Ries et al. |
| 5,326,367 | A | 7/1994 | Robioneck |
| 5,326,368 | A * | 7/1994 | Collazo ............ A61F 2/30734 623/22.22 |
| 5,350,381 | A | 9/1994 | Melton |
| 5,358,532 | A | 10/1994 | Evans et al. |
| 5,370,703 | A | 12/1994 | Willert et al. |
| 5,376,123 | A * | 12/1994 | Klaue ................ A61B 17/8841 623/23.19 |
| 5,387,241 | A * | 2/1995 | Hayes ................. A61F 2/30734 623/20.16 |
| 5,405,005 | A | 4/1995 | White |
| 5,405,392 | A | 4/1995 | Deckner |
| 5,456,717 | A | 10/1995 | Zweymuller et al. |
| 5,507,825 | A | 4/1996 | Frei |
| 5,507,830 | A | 4/1996 | Demane et al. |
| 5,549,702 | A | 8/1996 | Ries et al. |
| 5,571,105 | A | 11/1996 | Gundolf |
| 5,571,204 | A * | 11/1996 | Nies .................... A61F 2/30723 623/23.19 |
| 5,593,446 | A | 1/1997 | Kuoni |
| 5,641,323 | A | 6/1997 | Caldarise et al. |
| 5,676,704 | A | 10/1997 | Ries et al. |
| 5,755,720 | A | 5/1998 | Mikhail |
| 5,755,793 | A | 5/1998 | Smith et al. |
| 5,782,928 | A | 7/1998 | Ries et al. |
| 5,874,123 | A | 2/1999 | Park |
| 5,879,405 | A | 3/1999 | Ries et al. |
| 5,916,270 | A | 6/1999 | Lipman |
| 5,928,288 | A | 7/1999 | Wilson |
| 5,931,870 | A | 8/1999 | Cuckler et al. |
| 5,997,576 | A * | 12/1999 | Copf ................. A61B 17/7098 623/18.11 |
| 6,059,833 | A | 5/2000 | Doets |
| 6,066,154 | A * | 5/2000 | Reiley ............... A61B 17/7097 606/192 |
| 6,066,176 | A | 5/2000 | Oshida |
| 6,136,037 | A | 10/2000 | Hassig et al. |
| 6,162,227 | A | 12/2000 | Eckhardt et al. |
| 6,270,502 | B1 | 8/2001 | Stulberg |
| 6,325,829 | B1 | 12/2001 | Schmotzer |
| 6,344,060 | B1 | 2/2002 | Schmotzer et al. |
| 6,383,228 | B1 | 5/2002 | Schmotzer |
| 6,436,147 | B1 | 8/2002 | Zweymuller |
| 6,451,058 | B2 | 9/2002 | Tuke et al. |
| RE38,058 | E | 4/2003 | Fallin |
| 6,540,788 | B1 | 4/2003 | Zweymuller |
| 6,613,094 | B2 | 9/2003 | Zweymuller |
| 6,626,913 | B1 | 9/2003 | McKinnon et al. |
| 6,652,589 | B2 | 11/2003 | Schmotzer et al. |
| 6,692,529 | B2 * | 2/2004 | Shah .................. A61F 2/30728 623/22.13 |
| 6,746,452 | B2 | 6/2004 | Tuke et al. |
| 6,808,539 | B2 | 10/2004 | Zweymuller |
| 6,896,702 | B2 * | 5/2005 | Collazo ............ A61F 2/30734 623/20.16 |
| 6,916,342 | B2 | 7/2005 | Frederick et al. |
| 6,986,792 | B2 | 1/2006 | McLean et al. |
| 7,004,973 | B2 | 2/2006 | Zweymuller |
| 7,074,241 | B2 | 7/2006 | McKinnon |
| 7,160,307 | B2 | 1/2007 | Harwood et al. |
| 7,160,332 | B2 | 1/2007 | Frederick et al. |
| 7,175,664 | B1 | 2/2007 | Lakin |
| 7,175,668 | B2 | 2/2007 | Zweymuller |
| 7,179,297 | B2 | 2/2007 | McLean |
| 7,250,054 | B2 | 7/2007 | Allen et al. |
| 7,255,701 | B2 | 8/2007 | Allen et al. |
| 7,335,231 | B2 | 2/2008 | McLean |
| 7,374,576 | B1 | 5/2008 | Ries et al. |
| 7,455,693 | B2 | 11/2008 | Zweymuller |
| 7,494,510 | B2 | 2/2009 | Zweymuller |
| 7,497,875 | B1 | 3/2009 | Zweymuller |
| 7,534,271 | B2 | 5/2009 | Ries et al. |
| 7,575,603 | B2 | 8/2009 | Bergin et al. |
| 7,591,821 | B2 | 9/2009 | Kelman |
| 7,621,915 | B2 | 11/2009 | Frederick et al. |
| 7,682,398 | B2 | 3/2010 | Croxton et al. |

(56) References Cited

U.S. PATENT DOCUMENTS

| | | | |
|---|---|---|---|
| 7,749,277 B2 | 7/2010 | McLean | |
| 7,749,278 B2 | 7/2010 | Frederick et al. | |
| 7,780,667 B2 | 8/2010 | Watanabe et al. | |
| 7,828,806 B2 | 11/2010 | Graf et al. | |
| 7,842,095 B2 * | 11/2010 | Klein | A61F 2/36 606/94 |
| 7,862,619 B2 * | 1/2011 | Clark | A61F 2/38 623/20.3 |
| 7,863,410 B2 | 1/2011 | Smith et al. | |
| 7,879,106 B2 | 2/2011 | McMinn | |
| 7,892,290 B2 | 2/2011 | Bergin et al. | |
| 7,901,411 B2 | 3/2011 | Frederick et al. | |
| 7,985,260 B2 | 7/2011 | Keefer et al. | |
| 8,123,814 B2 | 2/2012 | Meridew et al. | |
| 8,226,727 B2 * | 7/2012 | Clark | A61F 2/389 623/20.36 |
| 8,268,383 B2 * | 9/2012 | Langhorn | A61F 2/30767 204/450 |
| 8,398,717 B2 * | 3/2013 | Kleinman | A61B 17/15 606/86 R |
| 8,454,706 B2 * | 6/2013 | de Beaubien | A61F 2/36 623/23.39 |
| 8,506,643 B2 | 8/2013 | Keefer et al. | |
| 8,551,181 B2 | 10/2013 | Meridew et al. | |
| 8,585,770 B2 * | 11/2013 | Meridew | A61F 2/30724 623/22.11 |
| 8,597,365 B2 | 12/2013 | Meridew | |
| 8,715,356 B2 | 5/2014 | Porter et al. | |
| 8,828,089 B1 | 9/2014 | Perez et al. | |
| 9,345,576 B2 * | 5/2016 | Shea | A61F 2/30734 |
| 2003/0060891 A1 * | 3/2003 | Shah | A61F 2/30728 623/22.13 |
| 2003/0065397 A1 | 4/2003 | Hanssen et al. | |
| 2003/0125809 A1 | 7/2003 | Iannotti et al. | |
| 2005/0021148 A1 | 1/2005 | Gibbs | |
| 2005/0049710 A1 | 3/2005 | O'Driscoll et al. | |
| 2006/0074430 A1 | 4/2006 | Deffenbaugh et al. | |
| 2007/0088443 A1 | 4/2007 | Hanssen et al. | |
| 2007/0250175 A1 | 10/2007 | Meridew et al. | |
| 2008/0021568 A1 | 1/2008 | Tulkis et al. | |
| 2009/0143824 A1 | 6/2009 | Austin et al. | |
| 2009/0204225 A1 * | 8/2009 | Meridew | A61F 2/30734 623/22.21 |
| 2009/0326670 A1 * | 12/2009 | Keefer | A61F 2/30734 623/22.22 |
| 2010/0161064 A1 | 6/2010 | Kellar et al. | |
| 2012/0016485 A1 | 1/2012 | Sharp | |
| 2012/0109137 A1 | 5/2012 | Iannotti et al. | |
| 2013/0338786 A1 | 12/2013 | Haidukewych | |
| 2014/0172113 A1 * | 6/2014 | Shea | A61F 2/30734 623/22.21 |
| 2014/0276870 A1 | 9/2014 | Eash | |
| 2014/0277529 A1 * | 9/2014 | Stalcup | A61F 2/38 623/20.16 |
| 2014/0343686 A1 | 11/2014 | Shea et al. | |
| 2015/0157462 A1 * | 6/2015 | Ek | A61F 2/4081 623/19.11 |
| 2016/0193051 A1 * | 7/2016 | Budhabhatti | A61F 2/30734 623/19.11 |

FOREIGN PATENT DOCUMENTS

| | | |
|---|---|---|
| FR | 2519248 A1 | 7/1983 |
| FR | 2633509 A1 | 1/1990 |
| JP | 2008532716 A | 8/2008 |
| JP | 2009502336 A | 1/2009 |
| JP | 2010012254 A | 1/2010 |
| JP | 2011511699 A | 4/2011 |
| WO | 20020083035 A2 | 10/2002 |
| WO | 2006099751 A1 | 9/2006 |
| WO | 2007014192 A2 | 2/2007 |

OTHER PUBLICATIONS

Australian Examination Report No. 1; Australian Patent Office; Australian Patent Application No. 2012347700; dated Oct. 14, 2016; 4 pages.
European Search Report; European Patent Office; European Patent Application No. 12854571.2; dated Jun. 26, 2015; 7 pages.
European Examination Report; European Patent Office; European Patent Application No. 12854571.2; dated Nov. 29, 2016; 4 pages.
Chinese Office Action; Chinese Patent Office; Chinese Patent Application No. 201280069283.4; dated Dec. 1, 2016; 13 pages.
European Examination Report; European Patent Office; European Patent Application No. 12855969.7; dated Jun. 28, 2016; 4 pages.
Chinese Search Report; Chinese Patent Office; Chinese Patent Application No. 201280069276.4; dated May 4, 2016; 4 pages.
Chinese Office Action; Chinese Patent Office; Chinese Patent Application No. 201280069276.4; dated May 13, 2016; 12 pages.
International Search Report and Written Opinion of Application No. PCT/US2012/088304, dated Mar. 25, 2013 (14 pages).
Japanese Notice of Reasons for Rejection; Japanese Patent Office; Japanese Patent Application No. 2014-546071; dated Sep. 26, 2016; 10 pages.
Japanese Notice of Reasons for Rejection; Japanese Patent Office; Japanese Patent Application No. 2014-546096; dated Oct. 3, 2016; 11 pages.
Chinese Office Action; Chinese Patent Office; Chinese Patent Application No. 201280069276.4; dated Feb. 13, 2017; 14 pages.
Australian Examination Report No. 2; Australian Patent Office; Australian Patent Application No. 2012347700; dated Jul. 20, 2017; 3 pages.
Australian Examination Report No. 2; Australian Patent Office; Australian Patent Application No. 2012347730; dated Aug. 7, 2017; 4 pages.
Japanese Decision of Rejection; Japanese Patent Office; Japanese Patent Application No. 2014-546071; Jul. 21, 2017; 5 pages.

* cited by examiner

ORTHOPEDIC AUGMENTS HAVING RECESSED POCKETS

This application is a continuation of U.S. patent application Ser. No. 14/185,444 filed Feb. 20, 2014, which is a U.S. national phase filing of International Application No. PCT/US2012/068304 filed Dec. 6, 2012, which claims the benefit of U.S. Provisional Patent Application No. 61/568,023 filed Dec. 7, 2011, the disclosures of each of these applications hereby incorporated by reference herein in their entirety.

BACKGROUND

Joints often undergo degenerative changes due to a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic materials, typically metals, ceramics, or plastics.

It may become necessary to conduct a second or subsequent surgery in order to replace a prosthetic joint with a (often larger) replacement joint. Such surgeries, known as "revision" surgeries, often occur due to further degeneration of bone or advancement of a degenerative disease, requiring removal of further bone and replacement of the removed, diseased bone with a larger or enhanced prosthetic joint, often referred to as a revision prosthesis. For example, bone is often lost around the rim of the acetabulum, and this may provide less rim coverage to securely place an acetabular cup.

In cases where the patient's bone around an implant is compromised, it may be necessary to utilize an augment to add additional support. For example, an acetabular augment may be placed to fill in a defect cavity around the acetabular shell to help support the loads transmitted to the shell. As part of the surgical technique, the surgeon may place both the shell and augment within the patient in order to ensure a proper fit before fastening the two components together to prevent motion between them. However, fastening the two components may be difficult, particularly when using bone cement, if the two components are congruent. Inadequate cementing between the components may cause them to separate after implantation, possibly causing particle generation and leading ultimately to revision.

In current augment designs no provision is typically given to assist with cement application. Therefore, surgeons apply the cement ad hoc (e.g., along the edges of the augment similar to a caulking bead) before fully assembling the components together or forgo the use of cement altogether. This leads to inconsistent and sometimes undesirable results with techniques that are not easily replicated.

SUMMARY

Disclosed herein are systems, devices, and methods for orthopedic augments having retaining pockets. In certain embodiments, the systems, devices, and methods include an orthopedic augment comprising an outer surface that interfaces with a patient's tissue or bone, and an inner surface that interfaces with an implant, the inner surface comprising a recessed pocket configured to receive a fixation material, a rim around at least a portion of the recessed pocket, and a port in the rim. The rim can mate with an implant. In certain embodiments, the recessed pocket extends along the inner surface in at least a direction laterally from the port. The port extends from the outer surface to the inner surface and thereby allows insertion of the fixation material into the recessed pocket.

In certain embodiments, the recessed pocket comprises a first compartment and a second compartment separated by a ridge. The ridge may be recessed relative to the rim. The fixation material rigidly affixes the augment to the implant. In certain embodiments, the fixation material is a cement or paste. In certain embodiments, the orthopedic augment further comprises a second port. The second port may be a fill gauge positioned inferiorly to the port, and the second port may have a geometry that is different than the geometry of the port. In certain embodiments, the port comprises a luer-lock fitting or a plug, and the port may be tapered. In certain embodiments, the orthopedic augment may further comprise an extension member configured to couple with an insertion device. The orthopedic augment may further comprise flanges, blades, hooks, or plates.

In certain embodiments, a surface of the augment is at least one of polished, matte, and porous. In certain embodiments, at least a portion of the outer surface comprises a polished finish. The outer surface may further comprise a matte finish or porous composition. In certain embodiments, the upper surface comprises a porous composition.

In certain embodiments, methods for implanting an orthopedic augment include placing an inner surface of the augment adjacent to an implant, wherein the inner surface comprises a recessed pocket and sport, and inserting a fixation material into the recessed pocket of the augment via the port, thereby affixing the augment to the implant. In certain embodiments, the inner surface of the augment further comprises a plurality of ports. The method may further include using at least one of the plurality of ports as a fill gauge, whereby the fixation material is injected into a first port until the fixation material is observed via a second port used as the fill gauge. The method may further include selecting a first port within which to inject the fixation material into the recessed pocket, and injecting the fixation material into the recessed pocket until the fixation element is observed passing a second port. In certain embodiments, the method includes determining a preferred orientation of the augment with respect to the implant and selecting, in response to the determining, one of the plurality of ports within which to inject the fixation material.

In certain embodiments, the recessed pocket comprises a first compartment and a second compartment. The port may be disposed proximate the first compartment. The method may further include injecting the fixation material into the first compartment via the port, wherein overfilling the first compartment causes the fixation material to flow into the second compartment. The fixation material may be a cement or paste and the implant may be an acetabular shell or cage.

In certain embodiments, a surface of the augment is at least one of polished, matte, and porous. In certain embodiments, at least a portion of the outer surface comprises a polished finish. The outer surface may further comprise a matte finish or porous composition. In certain embodiments, the upper surface comprises a porous composition.

In certain embodiments, a kit for use in orthopedic procedures is provided that includes a plurality of augments, each comprising a surface having a recessed pocket configured to receive a fixation material, a rim around at least a portion of the recessed pocket, and a port in the rim, wherein at least one of the plurality of augments has more than one port in the rim.

In certain embodiments, an orthopedic augment is provided that includes an outer surface that interfaces with a patient's tissue or bone, and an inner surface that interfaces with an implant, the inner surface comprising recessed means for receiving a fixation material, a rim around at least a portion of the recessed means, and access means in the rim, wherein the recessed means extend along the inner surface in at least a direction laterally from the access means.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, devices, and methods described herein, certain illustrative embodiments will be described. Although the embodiments and features described herein are specifically described for use in connection with acetabular systems, it will be understood that all the components, connection mechanisms, adjustable systems, manufacturing methods, coatings, and other features outlined below may be combined with one another in any suitable manner and may be adapted and applied to medical devices and implants to be used in other surgical procedures, including, but not limited to orthopedic knee replacement procedures, spine arthroplasty, cranio-maxillofacial surgical procedures, hip arthroplasty, shoulder arthroplasty, as well as foot, ankle, hand, and other extremity procedures.

The augments described herein provide a surgeon with unitization options to accommodate a wide variety of bone anatomies and implant structures. The augments preferably maintain a close interface with both an implant and a patient's surrounding bone or tissue while allowing the surgeon to place the augments in a variety of positions, either before or after implantation of the implant, in order to suit different bone anatomies and implant structures. In addition, the augments incorporate recessed pockets into which a fixation material, such as cement, may be deposited. The recessed pockets allow pressurized deposition of the fixation material into locations that provide improved bonding across a greater surface area between the augment and the implant to which the augment is coupled.

Figure 1A:
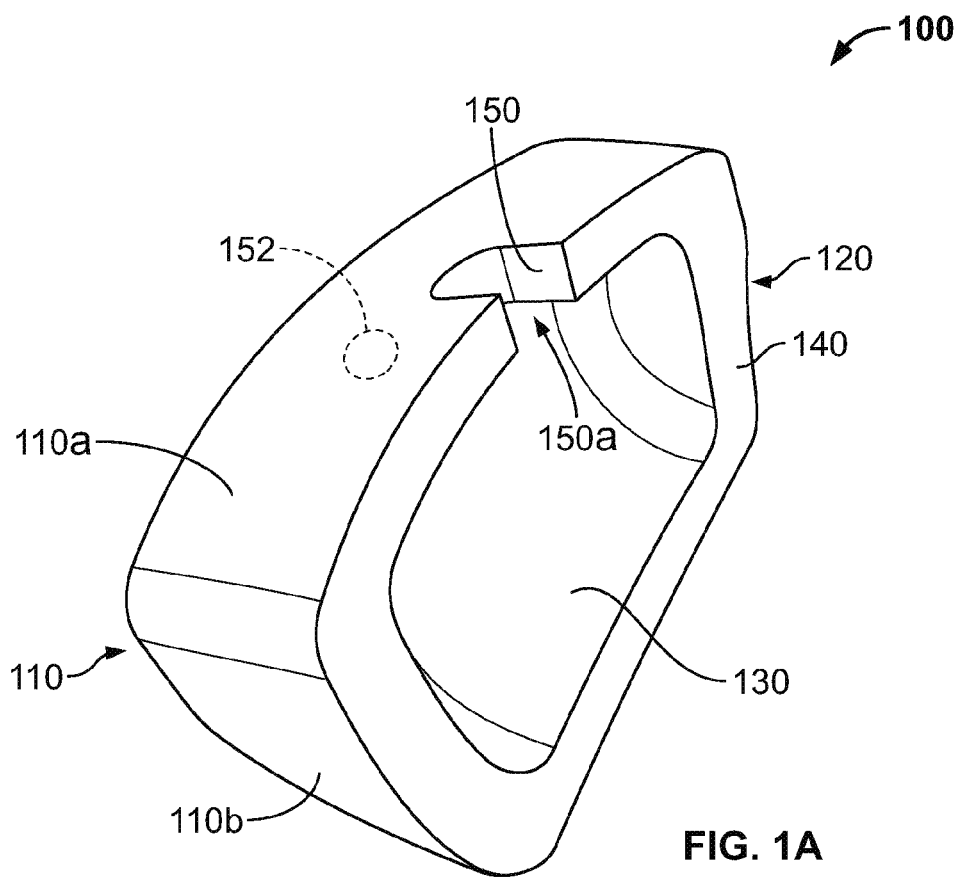
FIG. 1A shows a perspective view of an illustrative augment having a recessed pocket.

FIG. 1A shows a perspective view of an augment 100 having a recessed pocket 130 within an inner surface 120 of the augment 100. The augment 100 has an outer surface 110 that interfaces with a patient's tissue or bone and an inner surface 120 that interfaces with an implant. The inner surface 120 has a recessed pocket 130 formed therein that, as shown in FIG. 1A, occupies a substantial area of the inner surface 120 and is configured to receive a fixation material such as a cement or paste. When injected into the recessed pocket 130, the cement or paste affixes the augment 100 to an implant. Any suitable cement or paste may be used, including but not limited to polymethyl-methacrylate (PMMA), any other suitable biocompatible cement or paste, or other fixation material, or any combination thereof. In certain embodiments, the fixation material (e.g., PMMA) may be mixed with one or more pharmacological agents including, but not limited to, antibiotics, anti-inflammatory drugs, and growth factors.

The inner surface 120 also includes a rim 140 that mates with an implant and extends around at least a portion of the recessed pocket 130. As shown in FIG. 1A, for example, the rim 140 encircles the perimeter of the recessed pocket 130 along the periphery of the inner surface 120. When the augment 100 is positioned against an implant, the rim 140 substantially prevents a fixation material disposed in the recessed pocket 130 from leaving the recessed pocket 130. For example, the rim 140 is configured to mate with an implant and may be shaped so that the rim 140 matches the geometry of the implant and abuts the implant, which prevents a fixation material from leaving the recessed pocket 130. As shown in FIGS. 1C and 1D, the rim 140 has a curvilinear or arced shape to complement the shape of an implant 190 such as an acetabular shell. In certain embodiments, the rim 140 may be optionally coated with a resorbable or non-resorbable material such as a polylactic plastic (PLA) or PGA plastic. In certain embodiments, a gasket or other sealing means may be optionally provided between the rim of the augment and the implant. The gasket may help to contain the fixation material with the recessed pocket.

In order to allow a surgeon to inject or otherwise insert a fixation material into the recessed pocket 130, the inner surface 120 includes a port 150 within the rim 140 that extends from the outer surface 110 to the recessed pocket 130 of the inner surface 120. As shown in FIG. 1A, for example, the port 150 is disposed in the top of the rim 140 and extends from the superior outer surface 110a to the recessed pocket 130, thereby allowing a surgeon to inject a fixation material into the recessed pocket 130 when the augment 100 is mated with an implant. This can be done before or after the implant and augment have been implanted into a patient. The port 150 is shown as a half-circle or half-oval cutout made into the top of the rim 140 and having an open end 150a. In certain embodiments, a port may be provided as a through-hole made into the rim 140. For example, port 152 is provided as a through-hole in the rim 140. Alternatively, or additionally, in certain embodiments a port 154 may be provided as a through-hole in the outer surface 110 that accesses the recessed pocked 130 but is not disposed in the rim 140.

The port 150 assists with the injection of a fixation material into desired areas of the augment regardless of where the augment is positioned relative to the implant or whether the augment is affixed to the implant before or after the two components are implanted. Unlike current augment designs, where if the surgeon desires to use cement, the surgeon must first cement the augment to the implant before implantation, the recessed pockets described herein (such as recessed pocket 130) allow surgeons to place the augment adjacent to the implant in the desired location before or after implantation and then fill the recessed pocket with the fixation material via the port, thereby affixing the augment to the implant. Thus, the features of the augment 100 provide improved securement options for surgeons to implant augments before or after the acetabular shell or other implant has been implanted.

Figure 1B:
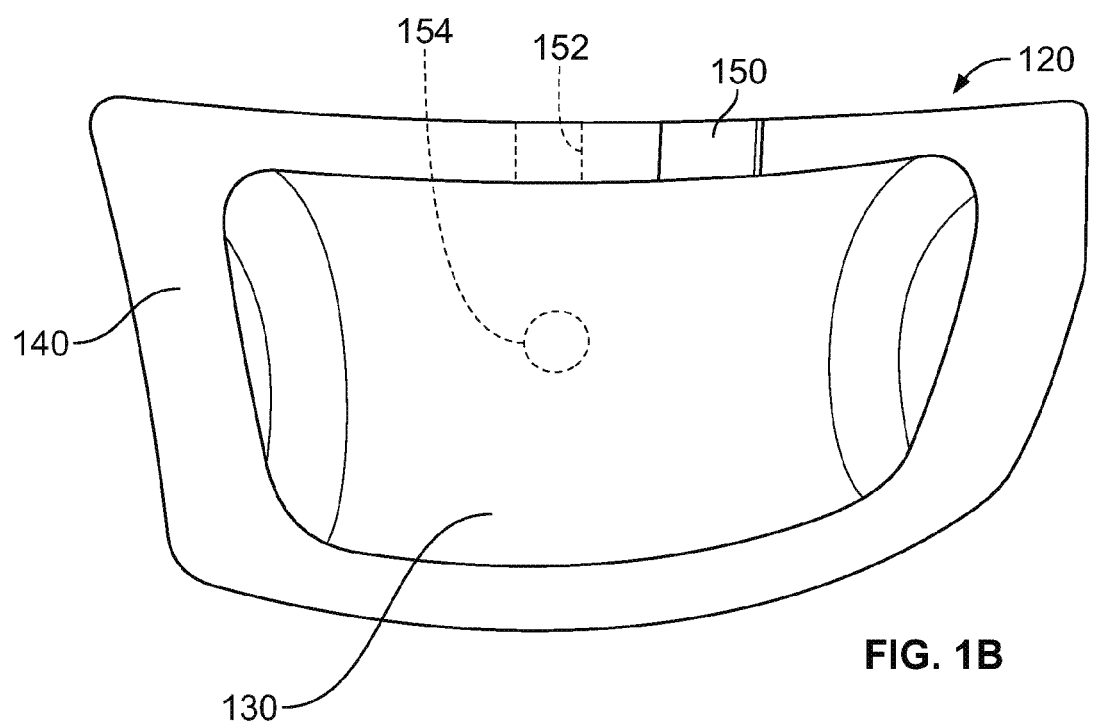
FIG. 1B shows a front elevation view of the illustrative augment of FIG. 1A.
Figure 1C:
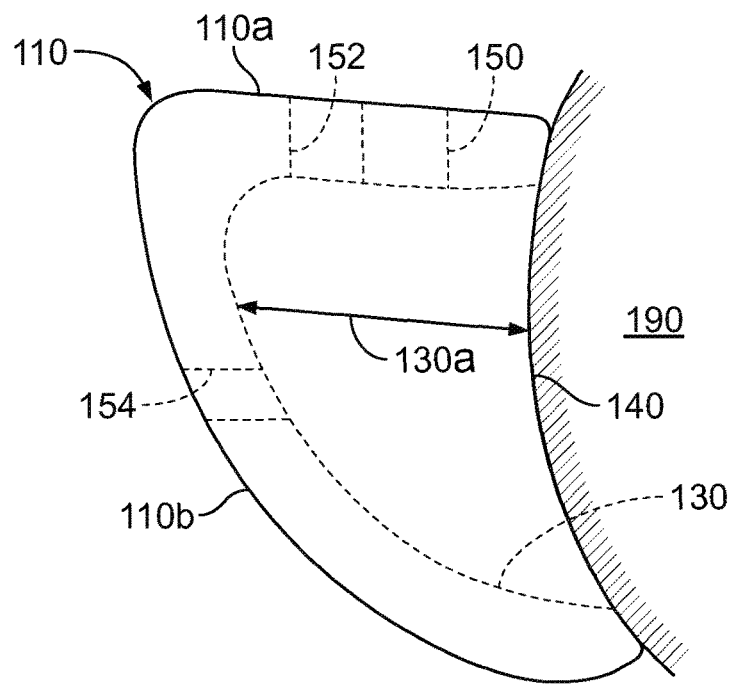
FIG. 1C shows a side elevation view of the illustrative augment of FIG. 1A adjacent to an implant.
Figure 1D:
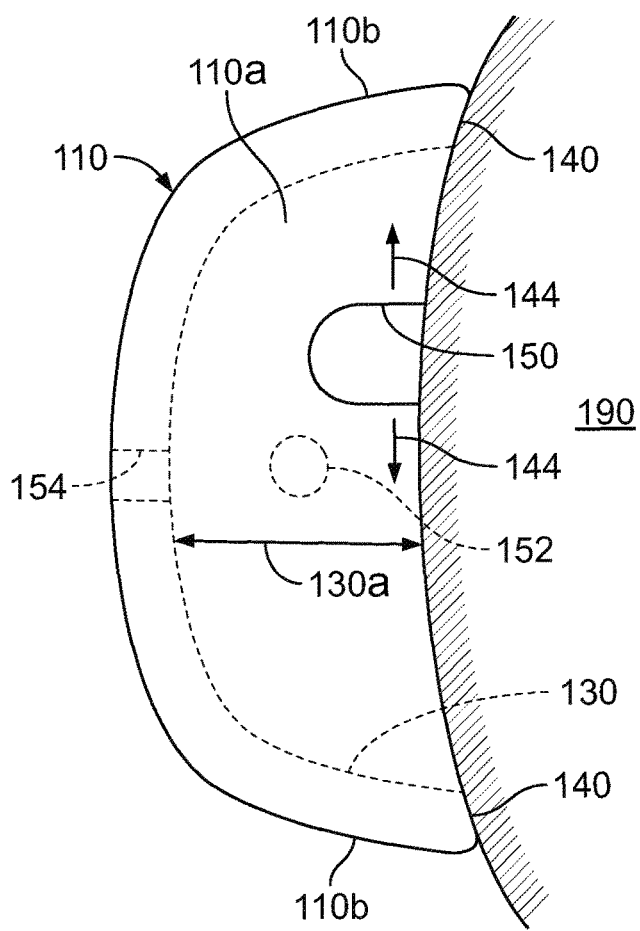
FIG. 1D shows a top plan view of the illustrative augment of FIG. 1A adjacent to an implant.

FIG. 1B shows a front elevation view of the inner surface 120 of the augment 100 of FIG. 1A, including the recessed pocket 130, the rim 140 that substantially encircles the recessed pocket 130, and the port 150 disposed on an upper portion of the rim 140. As shown in FIG. 1B, the recessed pocket 130 has a shape that conforms to the shape of the augment 100 itself, although in certain embodiments the recessed pocket 130 may have any suitable shape including shapes that may not comport with the shape of the augment 100, yet still fit within the inner surface 120 of the augment 100. The rim 140 extends around at least a portion of the recessed pocket 130 and, as shown in FIG. 1B, extends around the entirety of the recessed pocket 130. The rim 140 provides the surface with which the augment 100 mates with an implant and also prevents a fixation material within the recessed pocket 130 from leaving the pocket 130 when the augment is adjacent the implant. For example, in certain embodiments the rim 140 makes a fluid-tight seal with the surface of the implant. In certain embodiments, contact that does not create a fluid-tight seal may still be sufficient to prevent the fixation material from leaving the recessed pocket 130. Disposed within the upper portion of the rim 140 is the port 150 that provides access to the recessed pocket 130.

As discussed above, the lira 140 provides that portion of the inner surface 120 that contacts an orthopedic implant. FIG. 1C shows a side elevation view of the augment 100 of FIG. 1A adjacent to an implant 190. The rim 140 of the augment 100 mates with the implant 190 and is shaped to complement the shape of the implant 190. The rim 140 makes a substantially flush contact with the implant 190, which substantially prevents a fixation material within the recessed pocket 130 from leaving the recessed pocket 130. As discussed above, the recessed pocket 130 can have any suitable shape. The recessed pocket 130 can also be provided with any suitable depth, where the depth 130a depicted in FIG. 1C is the absolute depth of the pocket, as the depth varies with proximity to the rim 140. The depth 130a of the recessed pocket 130 is proportional to the amount of fixation material that may be deposited within the recessed pocket 130 to affix the augment 100 to the implant 190. In certain embodiments, it may be desirable to provide a recessed pocket 130 having a relatively large depth 130a. For example, the depth of the recessed pocket (e.g., depth 130a) may be designed as deep as possible without sacrificing the material strength of the augment or fixation material. Suitable depths include, for example, about 1-10 millimeters, about 2-5 millimeters, or about 2-3 millimeters.

Because the rim 140 mates substantially flush with the implant 190, one or more ports 150 are provided to give a surgeon access to the recessed pocket 130 in order to inject or otherwise insert the fixation material into the recessed pocket 130. FIG. 1D shows a top plan view of the augment 100 of FIG. 1C and depicts the port 150 disposed in the upper portion of the rim 140 and extending from the recessed pocket 130 to the superior outer surface 110a. Although only one port 150 is shown, it will be understood that any suitable number of ports may be provided and, moreover, that the ports may be provided on any suitable portion of the outer surface 110 of the augment 100. For example, although the port 150 is shown on the superior outer surface 110a, alternatively or additionally, ports may be provided on the lateral outer surfaces 110b and the inferior outer surface 110c.

As shown in FIGS. 1A-1D, the recessed pocket 130 extends beyond the opening created by the port 150. In particular, the recessed pocket 130 extends along the inner surface 120 in at least a direction laterally from the port 150, as depicted by the direction of arrows 144 of FIG. 1D. The recessed pocket 130 therefore has a volume that does not depend upon the size of the port 150. As shown in FIGS. 1C and 1D, the recessed pocket 130 also has a depth 130a that extends beyond the opening created by the port 150.

Figure 2:
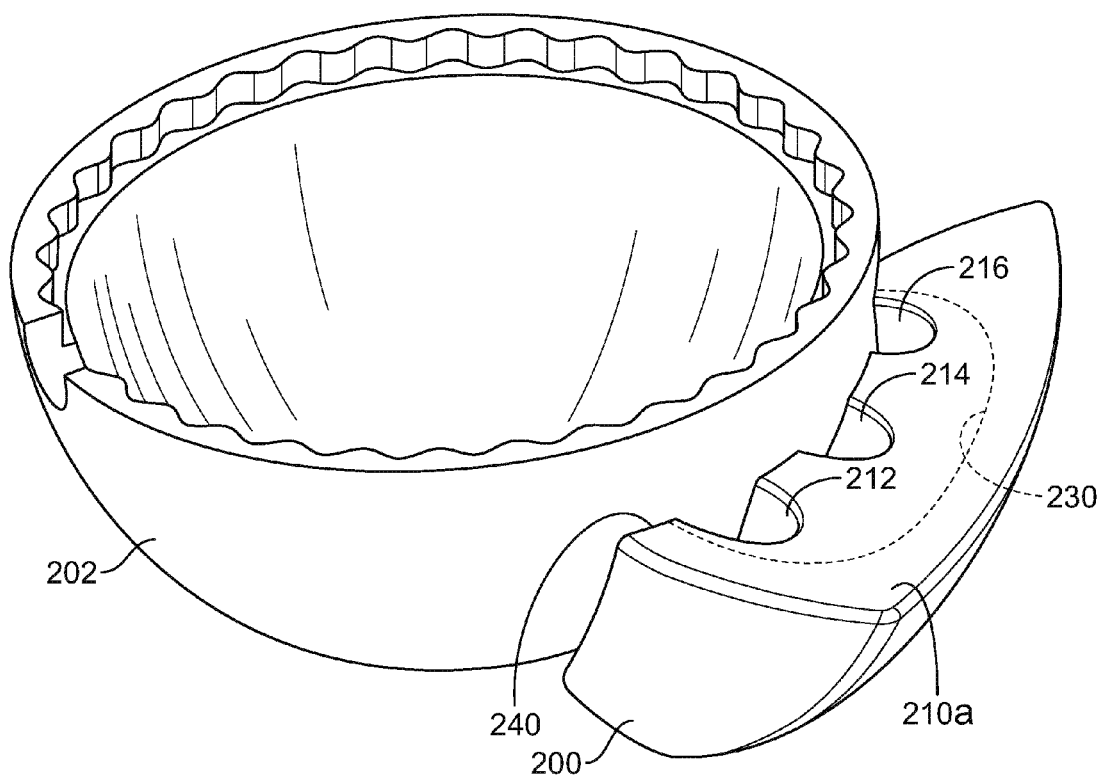
FIG. 2 shows a perspective view of an acetabular shell and an illustrative augment having a plurality of ports.

As discussed above, in certain configurations the augment may include more than one port. FIG. 2 shows a perspective view of an implant adjacent to an augment having multiple ports. In particular, FIG. 2 shows an implant 202, in this case an acetabular shell, and an augment 200 mated thereto and having three ports 212, 214, 216. The ports 212, 214, 216 are located on the superior outer surface 210a and extend through the top rim 240 of the augment 200. The augment 200 includes a recessed pocket 230, accessible from any of the ports 212, 214, 216. Providing multiple ports gives the surgeon the option, for example, to use any or all of them to inject a fixation material into the recessed pocket 230. For example, in certain embodiments, the operating window within which the surgeon works may be restricted so that one or more ports are not be accessible. However, because three ports 212, 214, 216 are provided, at least one of the ports may be accessible and the surgeon may fill the recessed pocket 230 by injecting a fixation material into that port. It will be understood that any suitable number of ports may be provided. For an augment having two or more ports, a surgeon would have similar options to use alternate ports if one or more ports are inaccessible for certain orientations of the augment with respect to an implant.

The above description applies to acetabular augments. However, similar recessed pockets could be applied to knee augments or other orthopedic implants where component are fixed together with a fixation material such as bone cement. An additional advantage of providing multiple ports is that a surgeon can inject the fixation material into one of the ports and use an unused port as a fill gauge to visually judge the amount of fixation material that has been injected into the augment. For example, as the recessed pocket is filled with fixation material, the surgeon can observe the fixation material through the unused port by looking into that port. This is helpful because the recessed pocket extends beyond the opening of the port. Numerous ports also give a surgeon the option to place the augment in any desired orientation, where at least one port is accessible from any orientation.

Figure 3A:
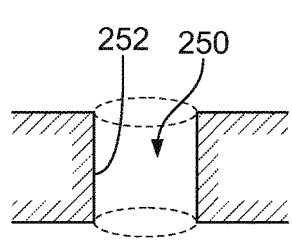
FIGS. 3A-3F show partial cross-sectional views of illustrative ports, and FIG. 3F also shows an illustrative insertion device coupled thereto.
Figure 3B:
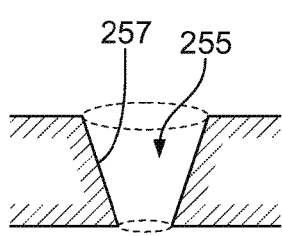
Figure 3C:
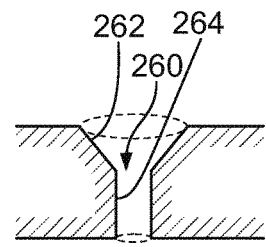
Figure 3D:
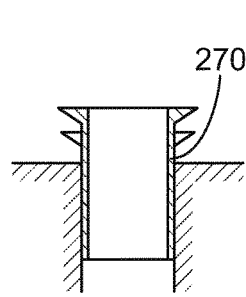
Figure 3E:
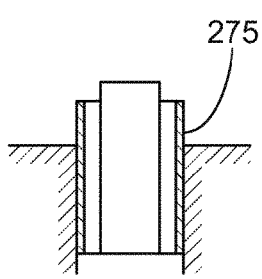
Figure 3F:
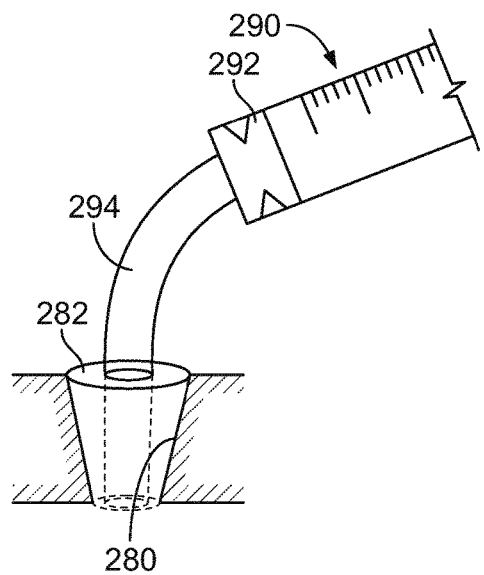

Although the ports 212, 214, 216 are shown as each having substantially the same geometry, it will be understood that any suitable geometry may be provided. For example, certain port geometries may be preferred for different types of syringes or other insertion devices used by the surgeon to inject a fixation material into the recessed pocket of an augment. As shown in FIG. 3A, a port 250 can have a straight-edge cut 252 through, for example, the outer surface of an augment. FIG. 3B shows that a port 255 can be tapered 257, while FIG. 3C shows a port 260 having both a tapered portion 262 and a straight-edge portion 264 to create a funnel-shaped port 260. In certain embodiments, any of ports 250, 255, 260 may be configured to include an integral lip at the upper surface for interfacing with an insertion device. In certain embodiments, the ports may include an insertion device fitting in order to assist with injection of the fixation material into the recessed pocket. A luer-lock type fitting, shown in FIGS. 3D (female luer-lock 270) and 3E (male luer-lock 275), or tapered plug 282, shown in FIG. 3F, may be incorporated into the port and outer surface so that a standard insertion device may be used, rather than requiring the surgeon to modify the insertion device. The insertion device fitting (e.g., the luer-lock or plug) allows for greater pressure to be generated, assisting with adequate flow of the fixation material into the gap between the augment and the implant and enhancing the fixation between the two components. In certain embodiments, both a plug and a luer-lock fitting are used. For example, as shown in FIG. 3F, in lieu of attaching the insertion device 290 directly to the plug 282 disposed within the port 280, an extension tube 294 coupled to the insertion device 290 via a luer-lock 292 is used. The extension tube 294 prevents interference, for example, from soft tissues proximate the port 280. In certain embodiments, the extension member such as extension tube 294 can have alternative fittings (e.g., other than the luer-lock 292) for various syringe types or other insertion devices.

Figure 4:
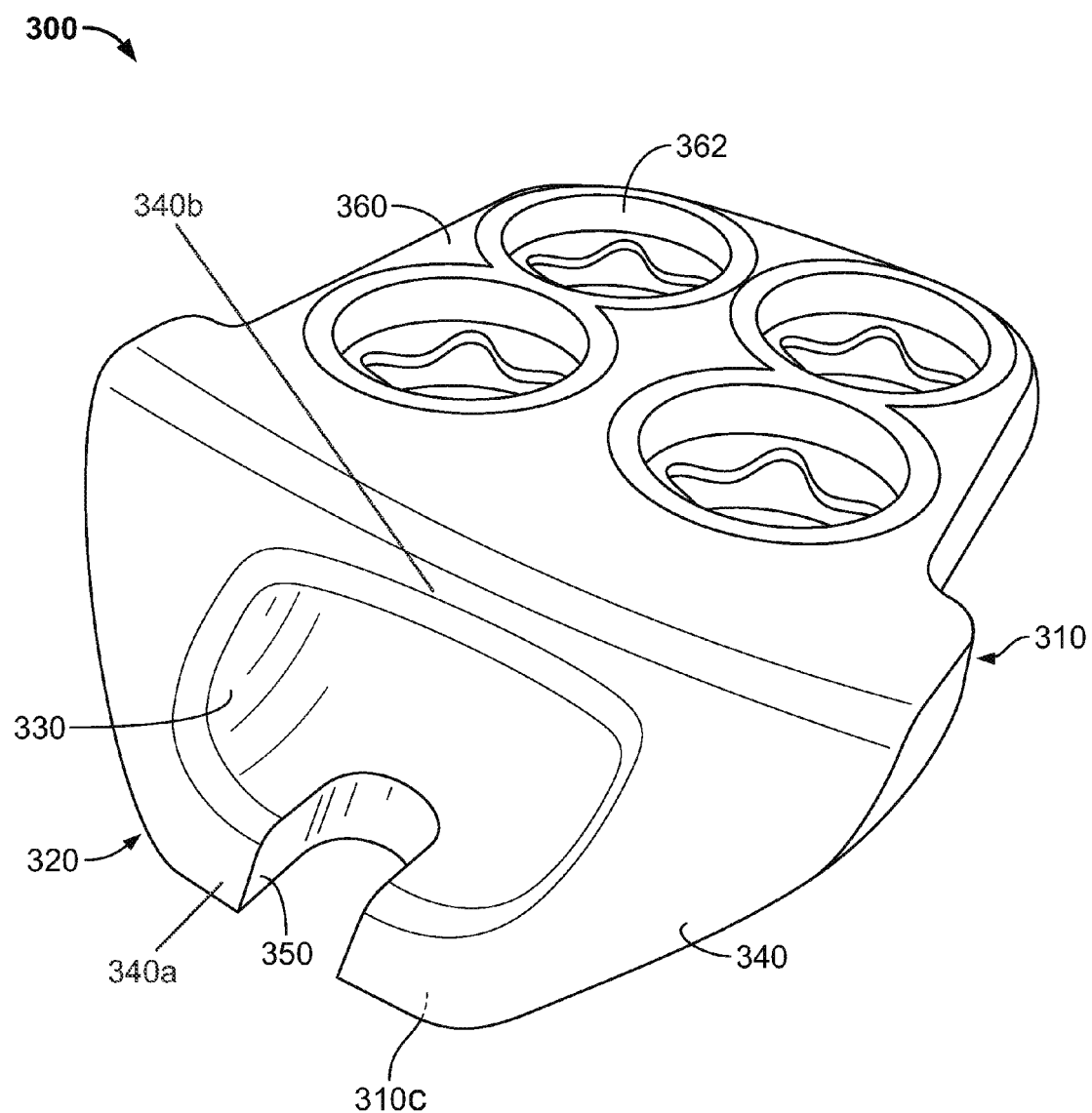
FIG. 4 shows a perspective view of an illustrative augment having a recessed pocket and a mounting member.

In addition to configurations of augments having multiple ports, in certain configurations, augments may include mounting members such as flanges, blades, hooks, plates, or any combination thereof, to assist with mounting the augment to the implant, the patient's tissue or bone, or both. Mounting members provide additional support and/or stability for the augment once positioned. Mounting members are often preferred due to bone degeneration, bone loss, or bone defects in the affected area (e.g., a hip joint). FIG. 4 shows a perspective view of an augment 300 having a mounting member 360. The mounting member 360 is a flange with one or a plurality of screw holes 362 configured to receive a fixation member such as a bone screw. In some embodiments, mounting members such as mounting member 360 may include conventional screw holes, locking holes, combi-holes, or slots. The sites may be threaded, unthreaded, or partially threaded, and may be fixed or polyaxial. In some embodiments, attachment sites may include variable low-profile holes that allow for locking at a variety of angles. The flange mounting member 360 is coupled to, and extends from, the outer surface 310 of the augment 300.

The inner surface 320 of the augment 300 has similar features as discussed above in connection with augment 100 of FIG. 1A, such as a recessed pocket 330 surrounded at least in part by a rim 340 and a port 350 therethrough that provides access to the recessed pocket 330. The port 350 is provided in the bottom 340a of the rim 340 and extends to the inferior outer surface 310c of the augment 300. It will be understood, however, that the port 350 (or additional ports, not depicted) could be provided on one or both lateral sides of the rim or on the top of the rim, similar to the location of the port 150 of FIG. 1A (e.g. along the top 340b of the rim, adjacent the mounting member 360 and the screw holes 362). Furthermore, in certain embodiments, one or more ports could be provided on a part of the outer surface 310 that provides access to the recessed pocket 330 without going through the rim 340 (e.g. through a back side of the pocket). As shown, the rim (e.g., rim 140 and 340) substantially encircles the perimeter of the recessed pocket and thereby provides a perimeter for the recessed pocket and a perimeter for the inner surface. In certain embodiments, however, the rim may not fully encircle the perimeter of the recessed pocket. For example, an augment may include multiple recessed pockets.

Figure 5A:
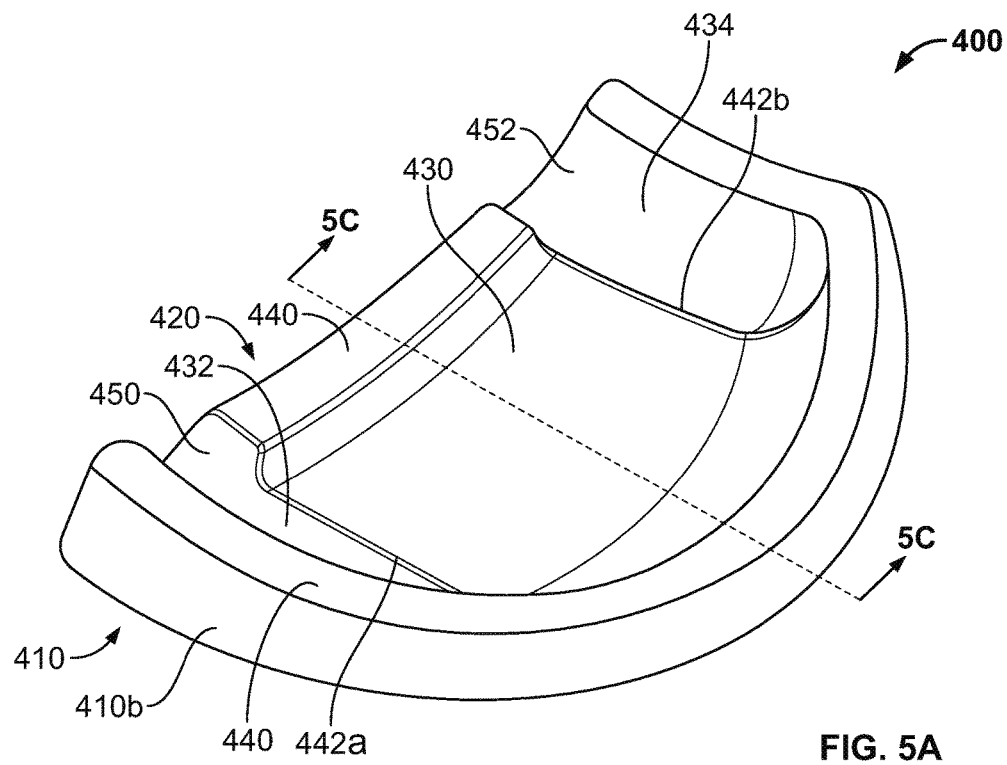
FIGS. 5A and 5B show perspective views of an illustrative augment having multiple recessed pockets.
Figure 5B:
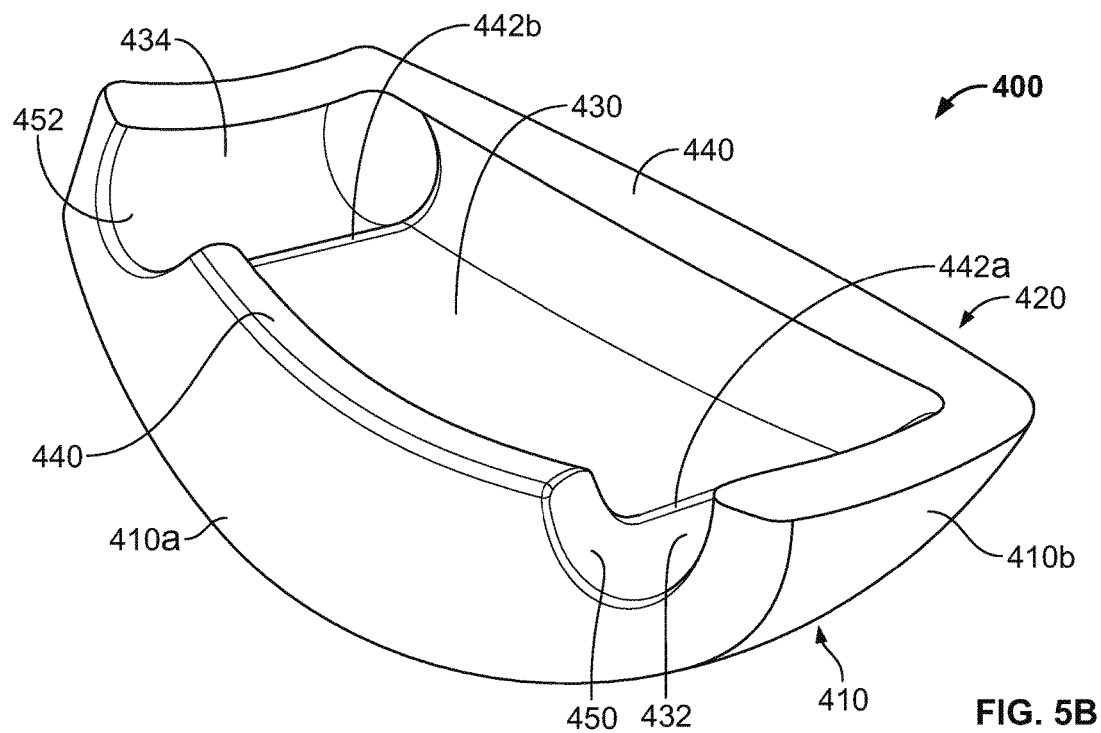

FIGS. 5A and 5B show perspective views of an augment having multiple recessed pockets. Multiple pockets give a surgeon various options during the procedure. For example, not every pocket need be filled with a fixation element. Furthermore, the pockets can be designed with different respective volumes depending, for example, on patient-specific or implant-specific applications. As shown in FIG. 5A, for example, the augment 400 includes an inner surface 420 having recessed pockets 430, 432, 434. The rim 440 of augment 400 is provided around at least a portion of each of the recessed pockets 430, 432, 434, although the rim 440 does not fully encircle the perimeter of any one recessed pocket 430, 432, 434. For example, the rim 440 provides an upper bound and a lower bound for the central recessed pocket 430, and provides a lateral bound for the lateral recessed pocket 432 and a lateral bound for the lateral recessed pocket 434. Disposed between the respective recessed pockets are ridges 442a and 442b. The ridges 442a and 442b do not extend as far as the rim 440, and therefore do not contact an implant when the augment 400 is placed adjacent to an implant (although in certain embodiments at least a portion of the ridges 442a and 442b could be configured to contact an implant). It will be understood that the ridges 442a and 442b may have any suitable respective height. The augment 400 includes two ports 450 and 452, where port 450 provides direct access to lateral recessed pocket 432 and port 452 provides direct access to lateral recessed pocket 434. Although there is no port shown that provides direct access to the central recessed pocket 430, overfilling either or both of the lateral recessed pockets 432, 434 via ports 450, 452 causes a fixation material to flow over the ridges 442a and 442b and thereby fill the central recessed pocket 430. Therefore, access can be provided to a plurality of recessed pockets that are separated by ridges, even in the event where only one recessed pocket has direct access to a port. In certain embodiments, the multiple recessed pockets could be provided without ridges between the pockets. For example, the augment could be provided with continuous and/or smooth portions between the pockets or have other ridges or protrusions along the inner surface 420 that grasp or otherwise provide a non-smooth structure with which the fixation material couples.

Figure 5C:
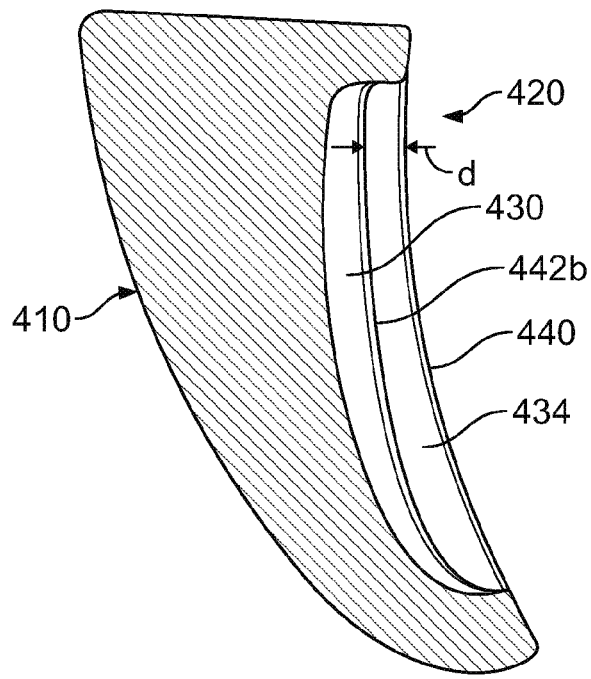
FIG. 5C shows a cross-sectional view of the illustrative augment of FIG. 5A, taken along line C-C.
Figure 5D:
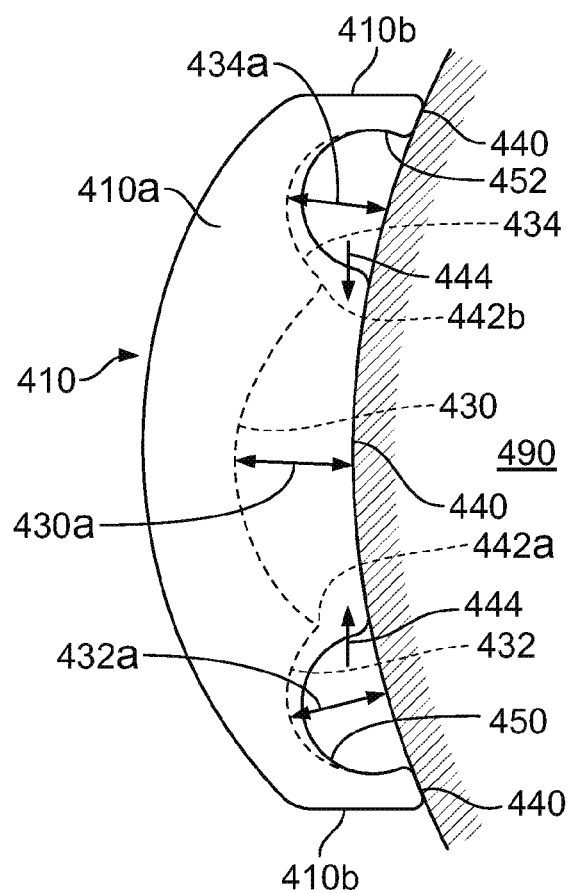
FIG. 5D shows a top plan view of the illustrative augment of FIGS. 5A and 5B adjacent to an implant.

FIG. 5B is a perspective view of the superior outer surface 410a and provides another view of the ports 450, 452. As can be seen in FIG. 5B, for example, the port 452 is shaped similarly to the recessed pocket 434 and provides, by use of the ridges 442a and 442b, indirect access to the central recessed pocket 430 and the lateral recessed pocket 432, whereby overfilling the lateral recessed pocket 434 would cause the fixation material to flow to the other recessed pockets 430, 432. As can also be seen in FIG. 5B, the rim 440 provides the contact surface against which an implant, is placed, whereas the ridges 442a and 442b are inset relative to the rim 440. The ridges 442a and 442b do not extend as far the rim 440 and do not contact the implant in order to allow the fixation material to overfill from pocket to pocket. For example, as shown in FIG. 5C, which is a cross-sectional view taken along line C-C of FIG. 5A, the central recessed pocket 430 of the augment 400 has the greatest depth relative to the rim 440, and the ridge 442b, located between the central recessed pocket 430 and the lateral recessed pocket 434, is inset relative to the rim 440 by a distance, d. The distance, d, between the rim 440 and the ridge 442b is the area through which the fixation material is overfilled and flows from pocket to pocket. The ridge 442b can be provided at any suitable distance, d, that is inset relative to the rim 440. FIG. 5D shows a top plan view of the augment 400 of FIGS. 5A and 5B. As shown, the ports 450 and 452 are provided on the superior outer surface 410a and each of the recessed pockets 430, 432. 432 has a respective depth from the edge of the rim 440, depicted by depths 430a, 432a, and 434a. Also shown are the ridges 442a and 442b that separate the respective pockets. FIG. 5D also shows that the rim 440 of the inner surface 410 abuts the implant 490, but the ridges 442a and 442b are inset and do not contact the implant 490.

As shown in FIGS. 5A-5D, the lateral recessed pockets 432, 434 extend beyond the opening created by the ports 450, 452. In particular, the lateral recessed pockets 432, 434 extend along the inner surface 420 in at least a direction laterally from the ports 450, 452, as depicted by the direction of arrows 444 of FIG. 5D. The central recessed pocket 430 does not have a port that provides direct access thereto. The recessed pockets 430, 432, 434 therefore have respective volumes that do not depend upon the size of the ports 450, 452. As shown in FIGS. 5C and 5D, the recessed pockets also have depths 430a, 432a, 434a that extend beyond the opening created by the ports 450, 452.

Figure 6A:
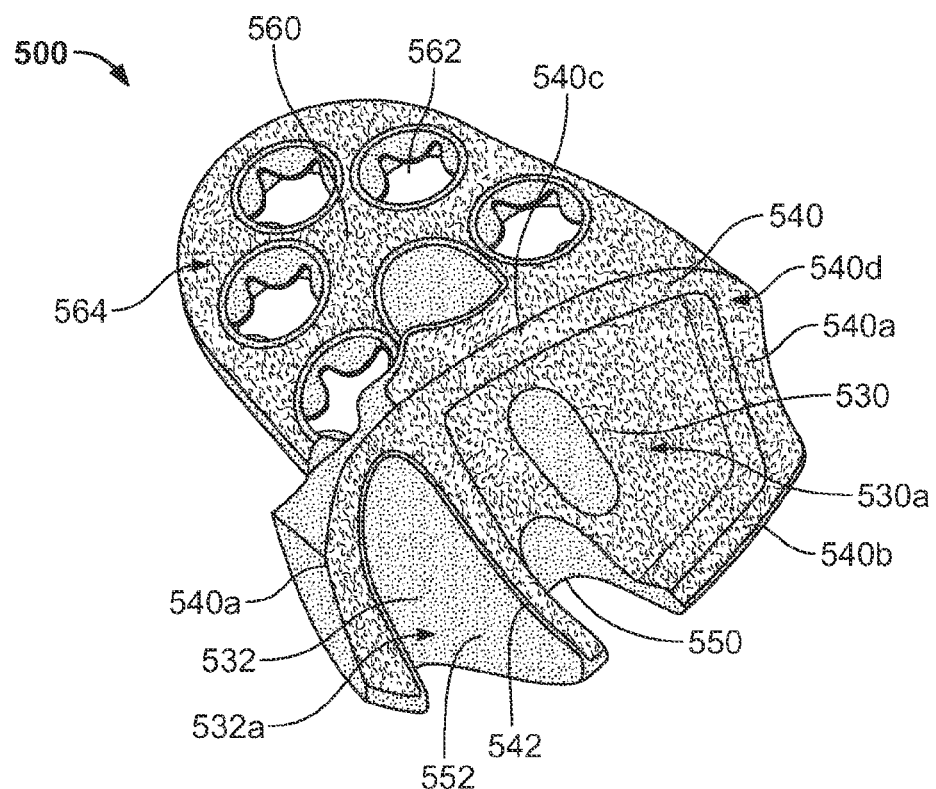
FIGS. 6A and 6B show perspective views of an illustrative augment having various surface finishes.
Figure 6B:
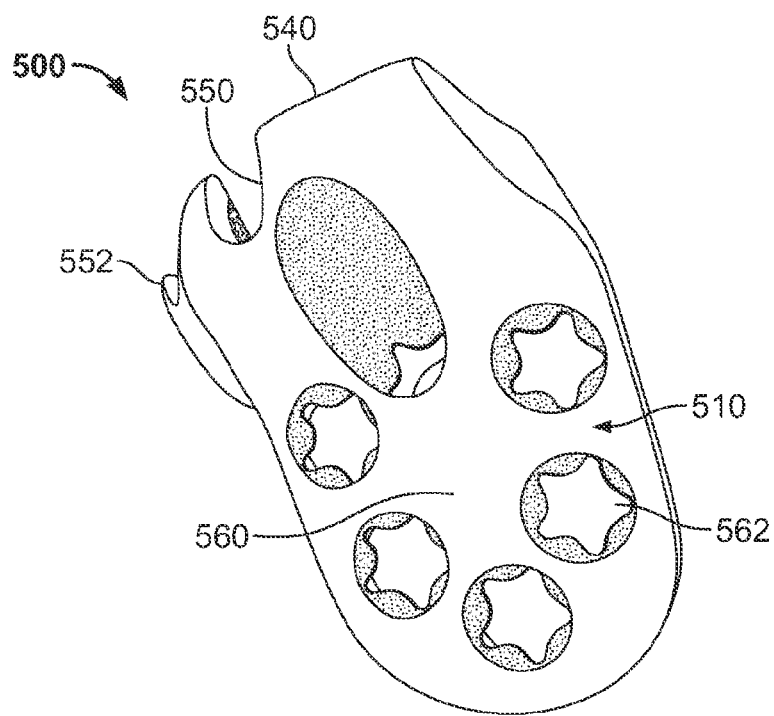

FIGS. 6A and 6B show perspective views of an augment 500 having various surface finishes. The augment 500 shown includes two recessed pockets 530 and 532 at least partially enclosed by a rim 540 and a mounting flange 560 extending from the augment 500. In certain embodiments, at least one of the recessed pockets is configured to accept a screw. For example, recessed pocket 532 may be configured to accept a screw. The recessed pockets 530 and 532 are separated at least in part by a ridge 542 and are accessible through ports 550 and 552, respectively. The ridge 542 has a height that does not extend as far as that of the rim 540, and therefore the ridge 542 does not contact an implant when the augment 500 is placed adjacent to the implant, such as implant 490. However, in certain embodiments, the ridge 542 can be extended to contact the implant 490. For example, the ridge 542 may have a height equal to or greater than that of rim 540. The ports 550 and 552 are shown as half circle or half oval cutouts made into the bottom 540b of the rim 540. It is understood, however, that one or more ports could be provided on any of the lateral sides 540a of the rim 540 or on the bottom 540b or top 540c of the rim 540, for example, as a through-hole or cut out made into the rim 540, or in any other suitable shape. Furthermore, in certain embodiments, one or more ports could be included on the outer surface 510 that provide access to the recessed pockets 530 and 532 without passing through the rim 540. The inner surface 530a of the recessed pocket 530 and surface 540d of the rim 540 are shown in FIG. 6A as having a porous composition, while the inner surface 532a of the recessed pocket 532 is shown as having a matte surface finish. The porous composition allows for better adhesion to fixation material such as cement or paste. The porous composition may interface with bone to promote ingrowth of the bone. In certain embodiments, the inner surfaces 530a and 532a in addition to the surface 540d of the rim 540 may include, at least in part, a variety of different surface treatments, compositions, or coatings. For example, the augment 500 shows a porous composition, a matte finish, and a polished finish on the back of the augment that extends to the mounting flange 560.

The mounting flange 560 extends outward from the augment 500 and includes six screw holes 562 configured to receive a fixation member such as a bone screw. In certain embodiments, any number of screw holes 562 may be included. As shown in FIGS. 6A and 6B, the mounting flange 560 has an upper surface 564 having a porous composition and a lower surface 510 having a polished finish. The porous upper surface 564 may receive a fixation material, and the polished lower surface 510 may be configured to interface with a patient's tissue, muscles, ligaments, or bone, or any combination thereof. The porous upper surface 564 is preferably configured to interface with bone and promote ingrowth of the bone. The polished lower surface 510 is preferably configured to interface with a patient's tissue, muscles, and/or ligaments to prevent interactions and attachments between the tissue, muscles, and/or ligaments and the polished lower surface 510. In certain embodiments, the upper surface 564 and lower surface 510 may include, at least in part, a variety of different surface treatments, compositions, or coatings. For example, the augment 500 shows a mounting flange 560 with a porous composition and a polished finish. Any other suitable combination of surface treatments may be used on various surfaces of the augment 500.

The augments described herein may be made of a number of materials, including Titanium, Cobalt-Chromium, Zirconium oxide, Stainless steel, monolithic ceramic or composite ceramic, such as Zirconia, Alumina, or other composites, or any other biocompatible materials or alloys that have the appropriate strength, resistance to wear, etc., or any combinations thereof. The augments may also be made fully porous or partially porous to allow for greater bone ingrowth, for example, and the augments may be coated with hydroxyapatite or any other bone-promoting agents or combinations thereof. The augments may be manufactured according to any suitable technique or techniques, including, for example, using rapid manufacturing machines or standard manufacturing machines.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to systems, devices, and methods to be used in other surgical procedures including, but not limited to, spine arthroplasty, cranio-maxillofacial surgical procedures, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method of utilizing an orthopedic augment structured for use with an orthopedic implant, wherein the augment is rigid and includes a porous outer surface, an inner surface defining a recessed pocket having a fixed shape, a port extending through the outer surface and the inner surface to the pocket, and a rim structured to flushly engage the implant, the method comprising:
   positioning the augment against the implant with the rim flushly engaged with the implant, thereby partially enclosing the pocket having the fixed shape; and
   affixing the augment to the implant with the rim flushly engaged with the implant, wherein the affixing includes inserting a fluid fixation material into the pocket via the port.

2. The method of claim 1, wherein the positioning and the affixing are performed with the implant implanted in a patient.

3. The method of claim 1, wherein the positioning includes forming a fluid-tight seal between the rim and the implant.

4. The method of claim 1, wherein the inserting of the fixation material into the pocket via the port includes injecting the fluid fixation material into the pocket via the port and filling the pocket with the fluid fixation material.

5. The method of claim 1, wherein a fitting is attached to the port, and wherein the method further comprises attaching an insertion device to the fitting prior to the affixing, and wherein the affixing includes operating the insertion device to inject the fluid fixation material into the pocket via the fitting.

6. The method of claim 1, wherein the augment comprises a plurality of ports, and wherein the affixing includes inserting the fluid fixation material into the pocket via a first of the ports until the fixation material is observed via a second of the ports.

7. The method of claim 1, wherein the augment comprises a plurality of ports, the method further comprising determining a preferred orientation of the augment with respect to the implant and selecting, based upon the determining, one of the plurality of ports through which to inject the fixation material; wherein the affixing includes injecting the fluid fixation material into the pocket via the selected port.

8. The method of claim 7, the fixation material is injected into the pocket via the selected port until the fixation material is observed via another of the ports.

9. The method of claim 1, wherein the pocket comprises a first compartment and a second compartment, wherein the fluid fixation material is injected into the first compartment via the port, and wherein overfilling the first compartment causes the fixation material to flow into the second compartment.

10. A method of utilizing an orthopedic augment structured for use with an orthopedic implant, wherein the augment includes a porous outer surface, an inner surface defining a recessed pocket, a port extending through the outer surface and the inner surface to the pocket, and a rim structured to flushly engage the implant, the method comprising:
   positioning the augment against the implant with the rim flushly engaged with the implant, wherein the positioning of the augment against the implant includes positioning a gasket between the rim and the implant such that the rim flushly engages the implant via the gasket; and
   affixing the augment to the implant with the rim flushly engaged with the implant, wherein the affixing includes inserting a fluid fixation material into the pocket via the port.

11. A method of utilizing an orthopedic augment structured for use with an orthopedic implant having a tissue-facing surface, wherein the augment includes an outer surface, an inner surface defining a recessed pocket, a port extending through the outer surface and the inner surface to the pocket, and a rim structured to flushly engage the tissue-facing surface of the implant, the method comprising:
   inserting the augment into a cavity of a surgical site, wherein the cavity is formed between a first portion of the tissue-facing surface and tissue defining a first surface of the surgical site, wherein a second portion of the tissue-facing surface is in contact with bone tissue defining a second surface of the surgical site, and wherein the inserting includes flushly engaging the rim with the first portion of the tissue-facing surface; and
   inserting a fixation material into the pocket of the augment via the port, thereby affixing the augment to the implant.

12. The method of claim 11, further comprising placing the implant at the surgical site such that the second portion of the tissue-facing surface contacts the bone tissue defining the second surface of the surgical site; wherein the placing of the implant is performed prior to the inserting of the augment into the cavity.

13. The method of claim 11, wherein the inserting of the augment is performed with the implant implanted at the surgical site.

14. The method of claim 11, wherein the inserting of the augment further comprises engaging the outer surface of the augment with the tissue defining the first surface of the surgical site.

15. The method of claim 14, wherein the tissue defining the first surface of the surgical site comprises soft tissue, and wherein the outer surface of the augment comprises a smooth surface finish configured to prevent attachment with the soft tissue.

16. The method of claim 14, wherein the tissue defining the first surface of the surgical site is defined by bone tissue, and wherein the outer surface of the augment comprises a porous composition configured to promote ingrowth of the bone tissue.

17. The method of claim 11, wherein one of the outer surface and the inner surface comprises a porous composition, and wherein the other of the outer surface and the inner surface comprises a smooth surface finish.

18. The method of claim 11, wherein the augment comprises a plurality of ports, and wherein the affixing includes inserting the fluid fixation material into the pocket via a first of the ports until the fixation material is observed via a second of the ports.

19. The method of claim 11, wherein the augment comprises a plurality of ports, the method further comprising determining a preferred orientation of the augment with respect to the implant and selecting, based upon the determining, one of the plurality of ports through which to inject the fixation material; wherein the affixing includes injecting the fluid fixation material into the pocket via the selected port.

20. The method of claim 19, wherein the fixation material is injected into the pocket via the selected port until the fixation material is observed via another of the ports.

* * * * *